United States Patent
Naba et al.

(10) Patent No.: US 8,807,750 B2
(45) Date of Patent: Aug. 19, 2014

(54) IMAGE ACQUISITION APPARATUS AND CONTROL METHOD THEREFOR

(75) Inventors: Takashi Naba, Kawasaki (JP); Kazuro Yamada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 247 days.

(21) Appl. No.: 13/174,999

(22) Filed: Jul. 1, 2011

(65) Prior Publication Data

US 2012/0013848 A1 Jan. 19, 2012

(30) Foreign Application Priority Data

Jul. 16, 2010 (JP) .................................. 2010-161373
Jun. 23, 2011 (JP) .................................. 2011-139041

(51) Int. Cl.
*A61B 3/14* (2006.01)
*A61B 3/00* (2006.01)

(52) U.S. Cl.
CPC ...................................... *A61B 3/14* (2013.01)
USPC ............................ 351/206; 351/209; 351/246

(58) Field of Classification Search
USPC .......................... 351/206, 209, 210, 221, 246
See application file for complete search history.

(56) References Cited

U.S. PATENT DOCUMENTS

| 7,557,931 | B2 | 7/2009 | Toida |
| 2007/0086011 | A1 | 4/2007 | Toida |
| 2009/0285354 | A1 | 11/2009 | Hirose et al. |
| 2010/0321700 | A1 | 12/2010 | Hirose et al. |
| 2011/0301455 | A1 | 12/2011 | Numajiri et al. |
| 2012/0230553 | A1* | 9/2012 | Chandra Bijalwan ........ 382/117 |

FOREIGN PATENT DOCUMENTS

| JP | 7-323011 A | 12/1995 |
| JP | 2007-101250 A | 4/2007 |

* cited by examiner

*Primary Examiner* — Jack Dinh
(74) *Attorney, Agent, or Firm* — Fitzpatrick, Cella, Harper & Scinto

(57) ABSTRACT

Provided is an image acquisition apparatus for acquiring a 3D retinal image with high resolution, which is capable of reducing a time period required for data transmission. In the image acquisition apparatus: a blink of a subject is detected; acquisition of image taking data is suspended thereafter until a line of sight becomes stable; and the data transmission to a computer is started at a timing at which a blink has been detected, thereby avoiding acquiring unnecessary data, allowing a capacity of a data buffer to be smaller, and making the data transmission efficient.

19 Claims, 6 Drawing Sheets

IMAGE ACQUISITION APPARATUS AND CONTROL METHOD THEREFOR

BACKGROUND OF THE INVENTION

1. Field of the Invention

The present invention relates to an image acquisition apparatus and a control method therefor. More particularly, the present invention relates to an image acquisition apparatus including an interference optical system, which is used for, for example, ophthalmologic diagnosis and treatment, and also relates to a control method therefor.

2. Description of the Related Art

Major examples of the currently-available ophthalmologic apparatuses which employ optical instruments include a confocal scanning laser ophthalmoscope (SLO) and an optical coherence tomography (OCT) apparatus (hereinbelow, referred to as OCT apparatus).

The OCT apparatus measures the state of a fundus with high sensitivity with the use of an interference beam obtained by irradiating a sample with a low coherence beam and then causing interference between the beam reflected from the sample and a reference light. In addition, by scanning the sample with the low coherence beam, the OCT apparatus is capable of acquiring, with high resolution, a tomographic image of the retina in the fundus of an eye to be inspected.

In general, there is used a tomographic image of the retina which is acquired through so-called B-scan by the OCT apparatus. This image is acquired by executing scan in a depth direction (Z-direction) of the retina, called A-scan, multiple times in an X-direction. With the B-scan, the internal state of the retina can be observed as well in the same way as in the case of using images obtained by the conventional fundus cameras or the like. Thus, it is possible to observe lesions inside the retina, in particular, macular degeneration and a macular hole. By taking multiple images through the B-scan in a Y-direction, a 3D retinal image is acquired, and this image is favorably used for observing the extent of a lesion and each layer inside the retina, particularly, for observing the ganglionic layer of optic nerve, which suffers glaucoma.

By the way, the conventional resolution in a lateral direction has been about 10 μm, but the resolution needs to be made higher when a capillary aneurysm or a photoreceptor cell is desired to be observed at the early stage of diabetes, for example. In this case, when optical resolution in the lateral direction is made higher, it is impossible for a single focusing point to achieve an in-focus state in a longitudinal direction across an entire area. To address this, image taking needs to be performed by using a technique called zone focusing, in which multiple focusing points are used.

Japanese Patent Application Laid-Open No. 2007-101250 discloses a basic configuration of the zone focusing. However, in this case, a large amount of data is acquired, and thus the image taking takes several tens of seconds. Hence, it is essential to take measures against the blink which occurs during this period.

As a measure taken for the fundus camera against the blink, Japanese Patent Application Laid-Open No. H07-323011 discloses a configuration in which, when a blink has been detected during the image taking, it is judged that data acquired during this period is unusable, and the data is deleted.

When the above-mentioned zone focusing is employed to take a 3D retinal image having a size of 10 mm ×10 mm with a lateral resolution of 3 μm and with the number of zones of 3, the data amount becomes about 20 Gbytes.

As for the time period required for the image taking, by using a so-called multibeam method in which multiple light sources and multiple line sensors are used to simultaneously acquire images of multiple portions, the data can be acquired in 30 to 40 seconds.

Further, when such data is transmitted to a computer for display and storage, it takes 40 seconds or longer to transmit the data even with a USB 3.0, which is the latest general-purpose data bus. In this case, because a data rate for the image taking is higher than a data transmission rate for communication, a communication data buffer having a capacity of 20 Gbytes is simply required. The data also needs to be transmitted after the data acquisition, and hence the data transmission takes more time than the image taking.

Further, there is a problem that, due to the blink, the time period required for the image taking becomes 1.2 times or longer, and that the data amount also becomes 1.2 times or larger, that is, 24 Gbytes or larger.

SUMMARY OF THE INVENTION

An object of the present invention is to address the above-mentioned problems, and to achieve reduction in time period required for image taking.

In order to solve the above-mentioned problems, an image acquisition apparatus according to the present invention includes: an acquisition unit for acquiring a tomographic image of an eye to be inspected; a control unit for transmitting the tomographic image to an external apparatus; a storing unit for storing the acquired tomographic image; and a detection unit for detecting a blink of the eye to be inspected, in which, when the detection unit detects the blink of the eye to be inspected, the control unit transmits the tomographic image stored in the storing unit to the external apparatus.

In other words, in an OCT apparatus for acquiring a 3D tomographic image by executing B-scan multiple times, the acquisition of data is suspended during a period after the blink of the eye of an image taking target is detected until the line of sight becomes stable thereafter, and when a blink has been detected again, the previously-acquired data is transmitted.

According to the present invention, the time period required for the image taking, including the data transmission, can be reduced.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

(First Embodiment)

Hereinbelow, an image acquisition apparatus according to a first embodiment of the present invention is described in detail with reference to the drawings.

Figure 1:
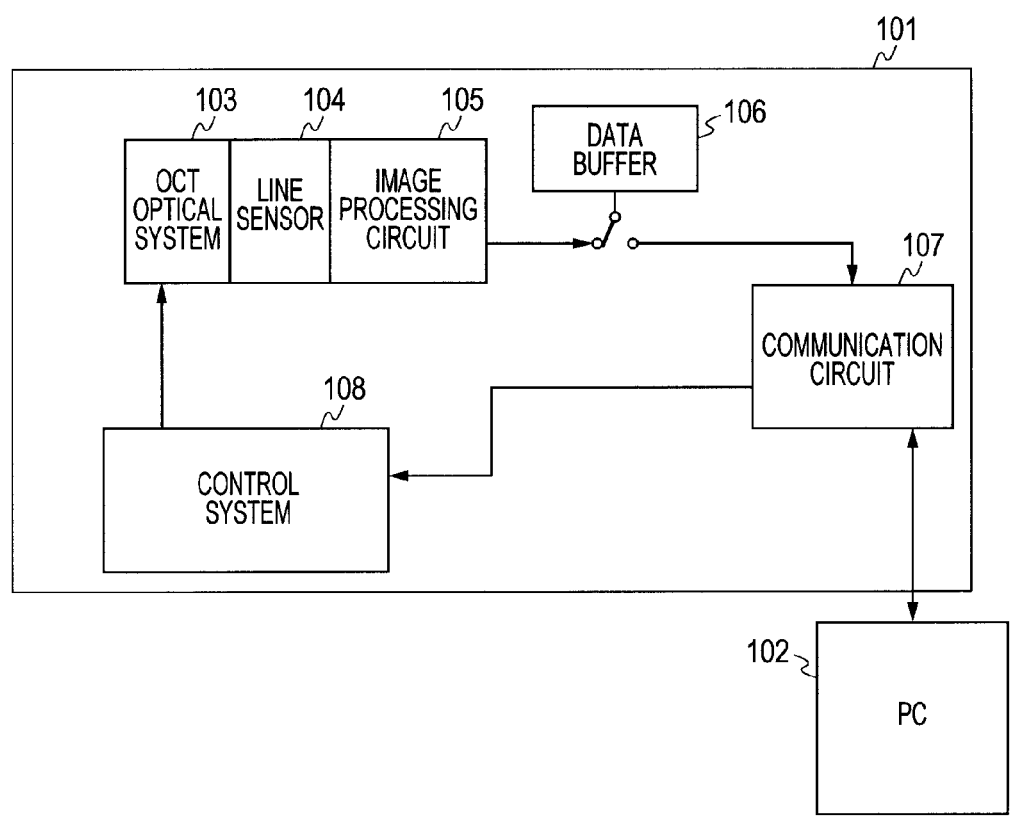
FIG. 1 is a block diagram illustrating a schematic configuration of an image acquisition apparatus according to a first embodiment of the present invention.
Figure 2:
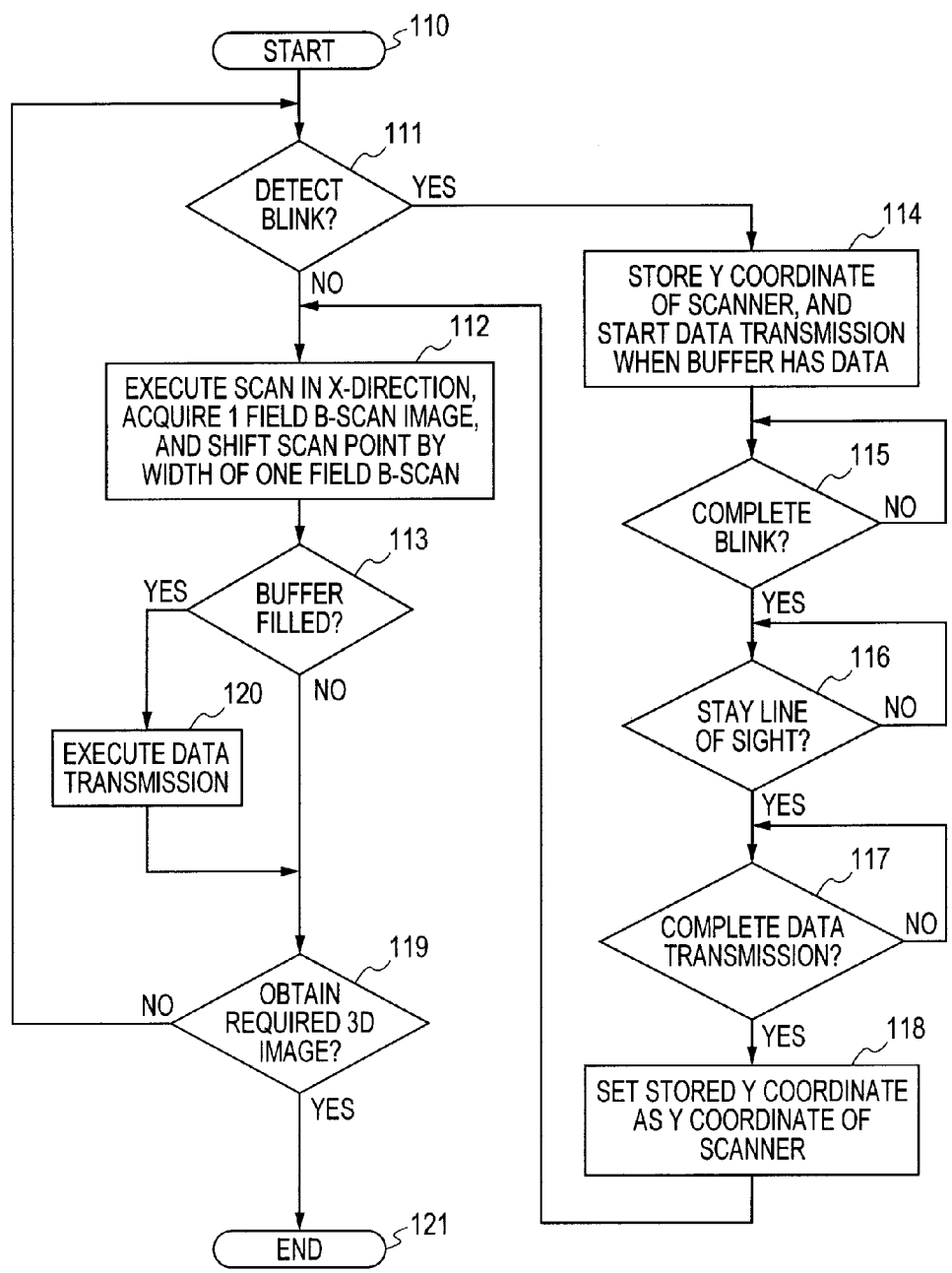
FIG. 2 is a flow chart illustrating processing performed at the time of image acquisition by the apparatus illustrated in FIG. 1.
Figure 3:
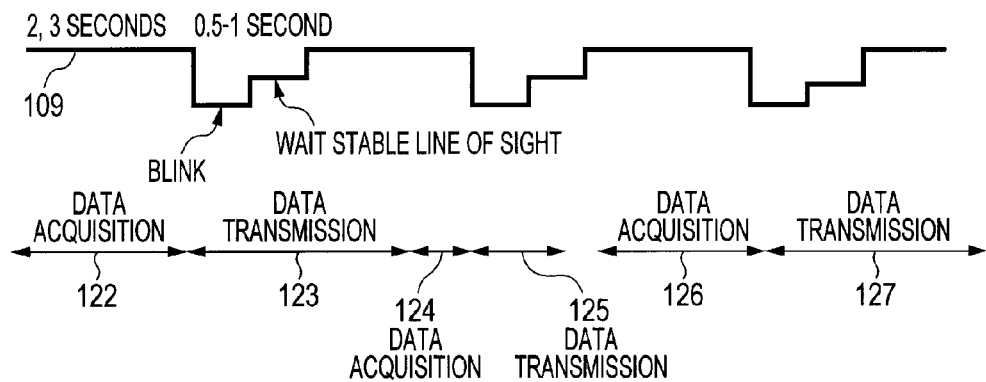
FIG. 3 is a timing chart illustrating operation timings used when the processing illustrated in FIG. 2 is performed.

FIG. 1 is a block diagram of an entire system of the image acquisition apparatus of this embodiment, FIG. 2 is a flow chart of processing operation according to this embodiment, and FIG. 3 is a timing chart of the processing operation according to this embodiment.

The image acquisition apparatus illustrated in FIG. 1 includes an optical coherence tomography (OCT) apparatus 101 and a computer 102 for controlling the image acquisition apparatus and other components relevant thereto and displaying and storing data acquired by image taking. The OCT apparatus 101 constitutes the image acquisition apparatus of the present invention which acquires a tomographic image of an eye to be inspected and transmits the tomographic image to the computer 102 being an external apparatus. The OCT apparatus 101 includes an OCT optical system 103, a line sensor 104, an image processing circuit 105, a data buffer 106, a communication circuit 107, and a control system 108 being a control unit. The OCT optical system 103 includes a scan unit (not shown) for scanning a fundus of the eye to be inspected with an inspection beam. The OCT optical system 103 splits a low coherence beam into a reference light and a signal beam being the inspection beam, generates an interference beam by causing, at an interference unit (not shown), the signal beam returning from the eye to be inspected and a return light being the reference light returning from a reference object to interfere with and be superimposed on each other, and disperses the interference beam into frequency components. The line sensor 104 being a light receiving unit receives the interference beam dispersed by the OCT optical system 103, and then converts the interference beam into an electric signal. The electric signal thus acquired is subjected to such processing as frequency/wavelength conversion and FFT by the image processing circuit 105, and is then converted into data in a depth direction of the retina. The image processing circuit 105 functions as a generation unit for generating the tomographic image based on the received interference beam. When data is processed in the case of zone focusing, only a piece of data corresponding to a target focus is extracted and is then temporarily stored in the data buffer 106. The data buffer 106 functions as a storing unit for storing the acquired tomographic image. The stored data is caused to pass through the communication circuit at a timing described later, and is then transmitted to the computer 102. Further, the control system 108 drives the scan unit (not shown) such as an XY scanner and a reference mirror (not shown) for changing the position of a coherence gate, which are provided in the optical system, executes a flow chart of FIG. 2 so as to acquire an interference waveform at a desired position of the retina, and receives an instruction to start operation from the computer 102.

Further, the data buffer has a capacity large enough to store data corresponding to about three seconds, which is an average time interval required for the blink and the line of sight to become stable. In a mode (20Gbytes for 30 to 40 seconds) described in this embodiment, a capacity of about 2 Gbytes is suitable.

The operation is described with reference to FIGS. 2 and 3. A movement 109 of the eye is illustrated in FIG. 3, in which: the upper side of the ordinate of the graph indicates a state in which the eye is opened; the lower side thereof indicates a state in which the eye is closed due to the blink; and the intermediate thereof indicates a state in which the line of sight is unstable due to the blink. The abscissa represents a flow of time in which time flows from left to right.

First, after the image taking is started in Step 110 of FIG. 2, it is checked in Step 111 whether or not a blink has occurred. Whether or not a blink has occurred can be checked by monitoring an output of the image processing circuit 105 and judging by the control system 108 or the computer 102 whether or not the output is equal to or larger than a threshold. Specifically, when a blink has occurred, there is no reflected beam from the retina, and hence interference does not occur. Accordingly, only noise components are acquired from the image processing circuit 105, with the result that a judgment can be made with ease. The configuration including the image processing circuit 105 and the control system 108 for monitoring the output therefrom functions as a detection unit for detecting the blink of the eye to be inspected according to the present invention.

When it is judged that no blink has occurred, B-scan is performed by the OCT apparatus 101 in Step 112, and the acquired image data or tomographic image is stored in the data buffer 106. Subsequently, the scanner is shifted in a Y-direction by the width of the B-scan. Then, in Step 113, when the storage area of the data buffer 106 is full, the connection destination of the data buffer 106 is switched to the communication circuit 107, and the image data is transmitted to the computer 102. Subsequently, in Step 119, it is checked whether or not image acquisition is completed. When the image acquisition is not completed, the processing returns to Step 111.

In Step 111, when a blink has been detected, the processing proceeds to Step 114. In Step 114, the control system 108 suspends the scan, thereby causing an acquisition unit to suspend the acquisition of the tomographic image. At the same time, the current Y coordinate of the scanner is stored, and when there is image data stored in the data buffer 106, the connection of the data buffer 106 is switched to the communication circuit 107, to thereby start to transmit the image data to the computer 102.

Subsequently, in Step 115, it is judged whether or not the blink has been completed. When it is judged that the blink has been completed, the flow proceeds to Step 116.

In Step 116, by using the above-mentioned detection unit, it is judged whether or not the line of sight has become stable. The judgment may be made based on the image data by the detection unit after the completion of the blink. Alternatively, considering that it normally takes about 0.2 to 0.3 seconds for the line of sight to become stable after the completion of the blink, a judgment may be made that the line of sight has become stable after a lapse of a predetermined period.

Here, a more accurate judgment can be made regarding whether or not the line of sight has become stable if the judgment is made as follows. That is, by using a function of correcting position displacement of the tomographic image, called tracking, the judgment regarding whether or not the line of sight has become stable is made based on whether or not the position displacement of the tomographic image can be corrected.

When it is judged in Step 116 that the line of sight has become stable, the flow subsequently proceeds to Step 117. In Step 117, it is judged whether or not the data transmission started in Step 114 has been completed, while waiting for the completion of the transmission. When the transmission has been completed, in Step 118, the connection destination of the data buffer 106 is switched to the output of the image processing circuit 105, and the Y coordinate of the XY scanner is set to the stored value.

Subsequently, the control system 108 returns to Step 112 and causes the B-scan to be resumed from the Y coordinate acquired before the blink. That is, in response to a judgment result indicating detection completion, which is a detection result indicating the completion of the blink, more specifically, after a judgment result indicating that the completion of the blink of the eye to be inspected has been detected is acquired, and further after the lapse of the predetermined period, the acquisition of the tomographic image by the acquisition unit is resumed. Further, the control system 108 records the scanning point (particularly, sub scanning point) of the scan unit acquired when the acquisition of the image data is suspended, and when the acquisition of the tomographic image is resumed, the acquisition of the image data is resumed from the scanning point thus recorded. Alternatively, the above-mentioned sub scanning point may be used to determine a sub scanning point for resuming the acquisition of the tomographic image. For example, when the above-mentioned sub scanning point is located in the vicinity of the center of a scan range, the acquisition of the tomographic image may be resumed from the vicinity of ⅓ of the scan range after transmitting the already-acquired image data. In general, the vicinity of the center of the scan range is an important part in terms of diagnosis. Thus, by resuming the sub scan (resuming the acquisition of the tomographic image) from the vicinity of ⅓ of the scan range, it is possible to prevent the tomographic image from failing to include the important part. Further, based on the above-mentioned sub scanning point, it may be judged whether or not the acquisition of the tomographic image is to be resumed. For example, when the above-mentioned sub scanning point is located past ⅔ of the scan range, after transmitting the already-acquired tomographic image, the processing may be finished without resuming the acquisition. In general, a marginal part of the scan range is not an important part in terms of diagnosis. Thus, it is not necessary to resume the acquisition of the tomographic image in the vicinity of a part located past ⅔ of the scan range. This reduces the time period required for the image taking. By repeating the operation described above, a desired 3D retinal image can be acquired. Note that, in this embodiment, after the lapse of the predetermined period after acquiring the judgment result, the acquisition of the tomographic image is resumed, but the condition for the resumption after acquiring the judgment result may be such other condition as the execution of further operation or the extent of change in image data.

Referring to FIG. 3, the above-mentioned operation is described. The image data acquired during a period 122, which is up until the blink is detected, is transmitted from the data buffer 106 to the computer 102 during a period 123 after the detection of the blink. While the image data is being transmitted, the blink becomes completed, and the line of sight becomes stable. After the transmission of the image data is completed, subsequent image data is acquired during a period 124, which is up until the next blink is detected, and the stored image data is transmitted again at a timing at which the blink has occurred (period 125). For example, in some cases, as indicated in the period 125, it is conceivable that the transmission of the image data is completed before the line of sight becomes stable. In this case, even if the data transmission is completed, the resumption of acquiring the image data is held on standby until the line of sight becomes stable. After the line of sight becomes stable, the acquisition of the subsequent image data is resumed (period 126). Subsequently, in response to the blink, the transmission of the image data during a period 127 and resumed acquisition are repeated. The operation described above is executed by the control system 108 being the control unit.

Specifically, a control method for the image acquisition apparatus according to the present invention includes an acquisition step of acquiring the tomographic image by the OCT apparatus and a storing step of storing the acquired tomographic image in the data buffer 106. Further, the control method further includes a detection step of detecting, by the detection unit, the blink of the eye to be inspected from which the tomographic image is being acquired, and a control step of starting, by the control system 108, the transmission of the image data from the data buffer 106 to the computer 102 in response to the detection of the blink of the eye to be inspected, which is made through the detection step.

With the operation described above, according to this embodiment, continuous pieces of image data can be acquired regardless of whether or not a blink has occurred, and the time period required for the image taking can be reduced compared to the conventional tomographic image taking performed in consideration of the blink. Further, the capacity of the data buffer can be made smaller compared to the conventional case. Further, unnecessary data, which is generated at the time of the blink and in a period thereafter until the line of sight becomes stable, is not acquired, and at the same time, this period is utilized to transmit data efficiently. In summary, a data buffer having a large capacity is not required because the image data obtained during the image taking is temporarily stored, and the data transmission can be made more efficient because unnecessary data is not acquired and transmitted.

(Second Embodiment)

In the first embodiment, the image taking cannot be performed during the data transmission because there is a single data buffer provided. In a second embodiment, two data buffers are used so that the data transmission and the storing of the image taking can be performed simultaneously.

Figure 4:
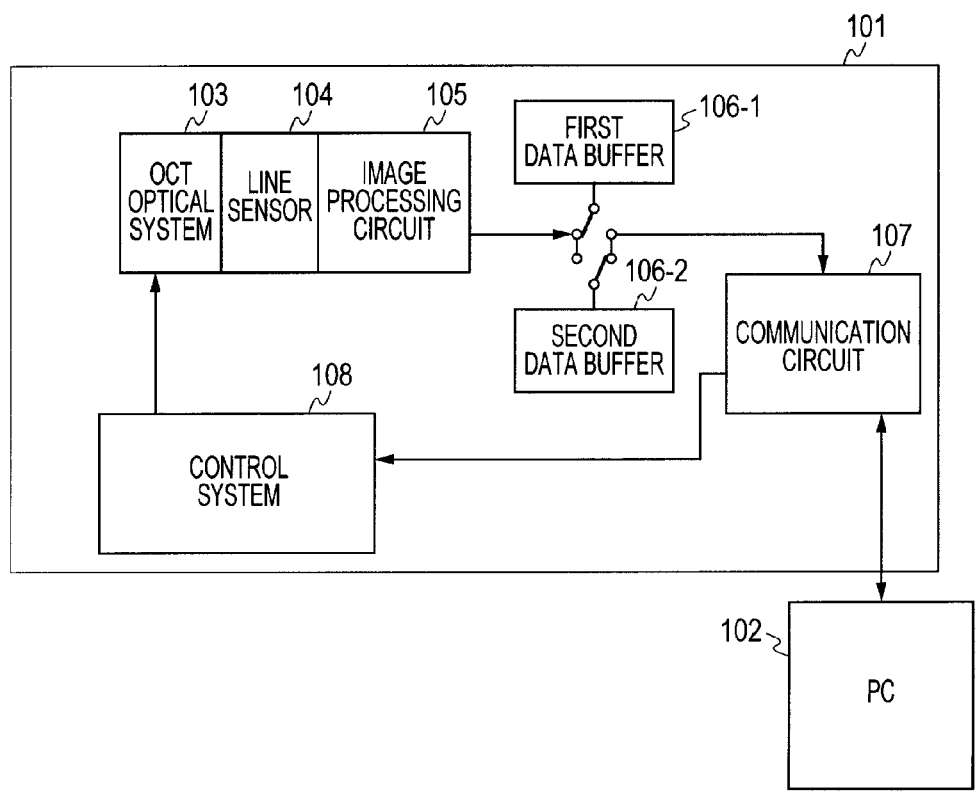
FIG. 4 is a block diagram illustrating a schematic configuration of an image acquisition apparatus according to a second embodiment of the present invention.
Figure 5:
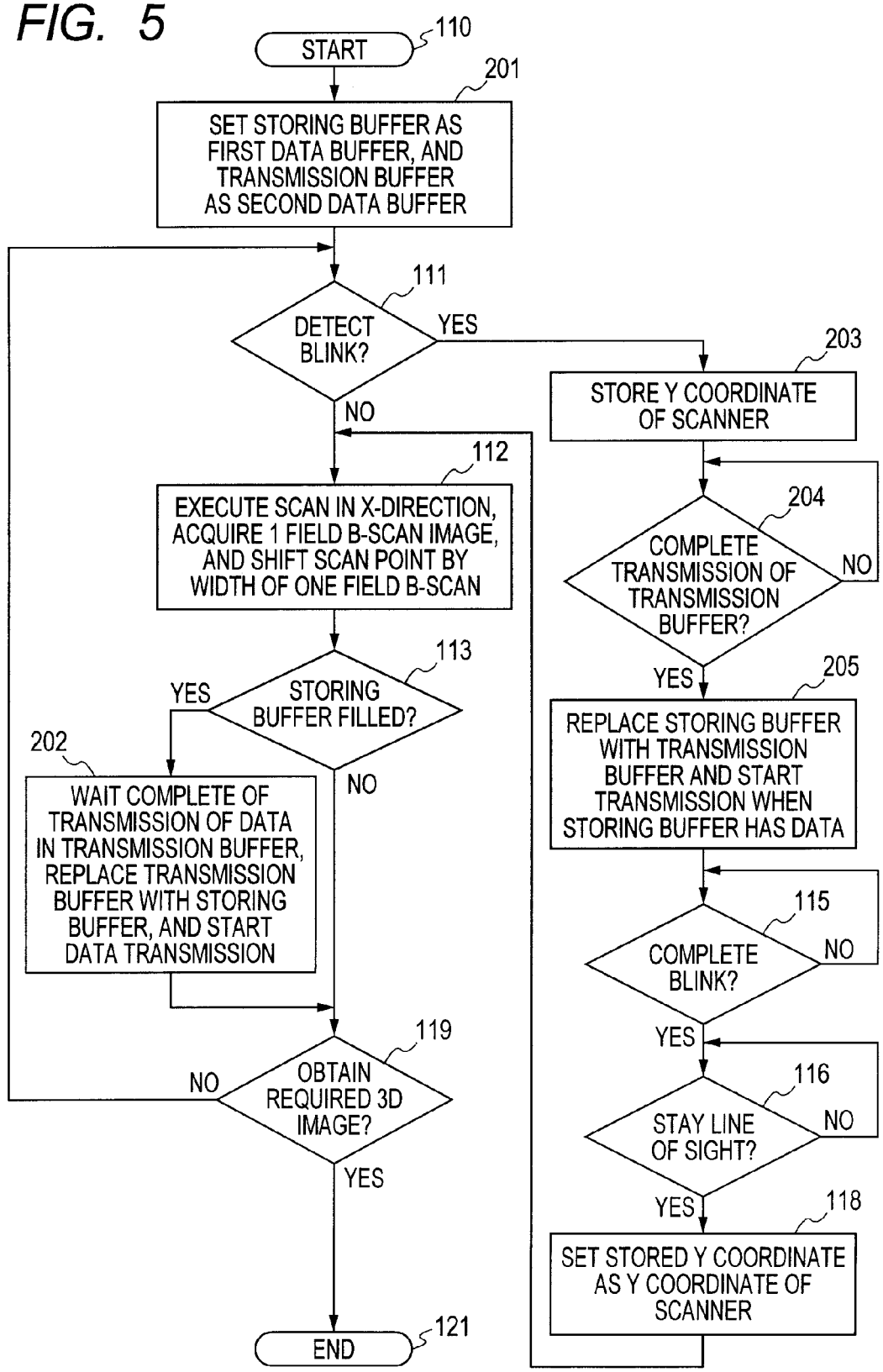
FIG. 5 is a flow chart illustrating processing performed at the time of image acquisition by the apparatus illustrated in FIG. 4.
Figure 6:
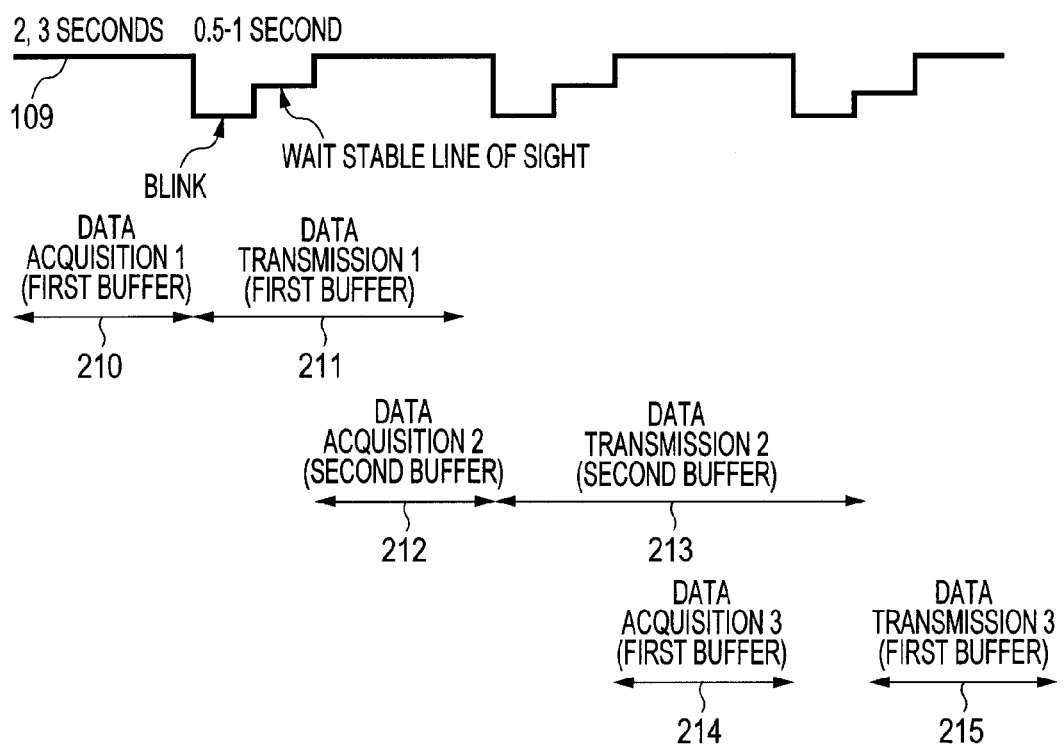
FIG. 6 is a timing chart illustrating operation timings used when the processing illustrated in FIG. 5 is performed.

FIG. 4 is a block diagram of an entire system of an image acquisition apparatus of this embodiment, FIG. 5 is a flow chart of processing operation according to this embodiment, and FIG. 6 is a timing chart of the processing operation according to this embodiment.

The only difference from the first embodiment is that, in the block diagram, a second data buffer 106-2 is additionally provided as well as a first data buffer 106-1. Referring to the flow chart, in comparison to the flow chart of the first embodiment: Step 201 is added; Step 120 is changed to Step 202; Step 114 is changed to Steps 203 and 205; and the processing of Step 117 is moved to the position of Step 204.

Hereinbelow, the difference is described in detail. In Step 201, the following processing is performed as initialization. That is, a buffer for storing is set as the first data buffer 106-1, and a buffer for data transmission is set as the second data buffer 106-2.

In Step 202, when the storing buffer has become full during the image taking, the transmission buffer and the storing buffer are replaced with each other so as to prevent the storing from being suspended.

Step 203 corresponds to part of the processing performed in Step 114 of the first embodiment, which is the processing of storing the current Y coordinate of the scanner. Step 204 is a step obtained by moving Step 117 of the first embodiment. However, there are two data buffers in this embodiment, and hence the image taking and the transmission can be performed simultaneously. This step is added because until one data buffer completes the processing of the image data transmission, the transmission of the subsequent image data by another data buffer needs to be held on standby.

In Step 205, the subsequent data transmission is started based on a judgment made in Step 204 that the preceding data transmission has been completed.

As in the first embodiment, referring to FIG. 6, start timings of the image data transmission and the like are described. Here, similarly to FIG. 3, FIG. 6 illustrates the movement 109 of the eye, in which: the upper side of the graph indicates the state in which the eye is opened; the lower side thereof indicates the state in which the eye is closed due to the blink; and the intermediate thereof indicates the state in which the line of sight after the blink is unstable.

During a period 210 up until a blink is detected, the acquired image data is stored in the first data buffer 106-1, and after a blink is detected, the first data buffer 106-1 is switched to be the transmission buffer, thereby starting the transmission of the image data, which is performed during a period 211. After the line of sight has become stable, the tomographic image taking is started, and the acquired data is stored in the second data buffer 106-2. Subsequently, in response to the detection of a blink, similarly, the second data buffer 106-2 is switched to be the transmission buffer, thereby starting the transmission of the image data from the second data buffer 106-2, which is performed during a period 213.

In parallel to the transmission of the image data from the second data buffer 106-2, the line of sight gradually becomes stable. After the line of sight has become stable, the storing of the image data indicated in a period 214, which uses the first data buffer 106-1 again, that is, the image taking is performed.

Here, as in the period 213, when the transmission of the image data is not completed after the blink, the completion of the transmission of the image data is awaited, and after a judgment that the transmission has been completed is made, the data transmission from the first data buffer 106-1 is performed as indicated in a period 215.

According to the configuration of this embodiment and the operation embodied by the configuration, the image taking and the data transmission can be performed without suspending the image taking because two data buffers are provided so that the image taking and storing of the image data and the transmission are performed alternately at timings at which the blink occurs and at which the line of sight becomes stable.

(Third Embodiment)

When the scanner executes the scan in an X-direction, a B-scan image (tomographic image) for one field is acquired. When a blink has occurred during the above-mentioned acquisition, the B-scan image for one field cannot be used. In the first and second embodiments, data is not transmitted to the PC in units of the B-scan image for one field. Instead, all data stored in the buffer is transmitted. The PC is capable of recognizing the occurrence of a blink from the fact that data contains noise components, and knows a data amount for one B-scan field. Thus, the B-scan image for one field obtained when a blink has occurred can be ignored, but the load imposed on the PC is large for this reason. In a third embodiment, only B-scan data obtained when no blink has occurred is transmitted to the PC on a field basis so as to reduce the load imposed on the PC.

Figure 7:
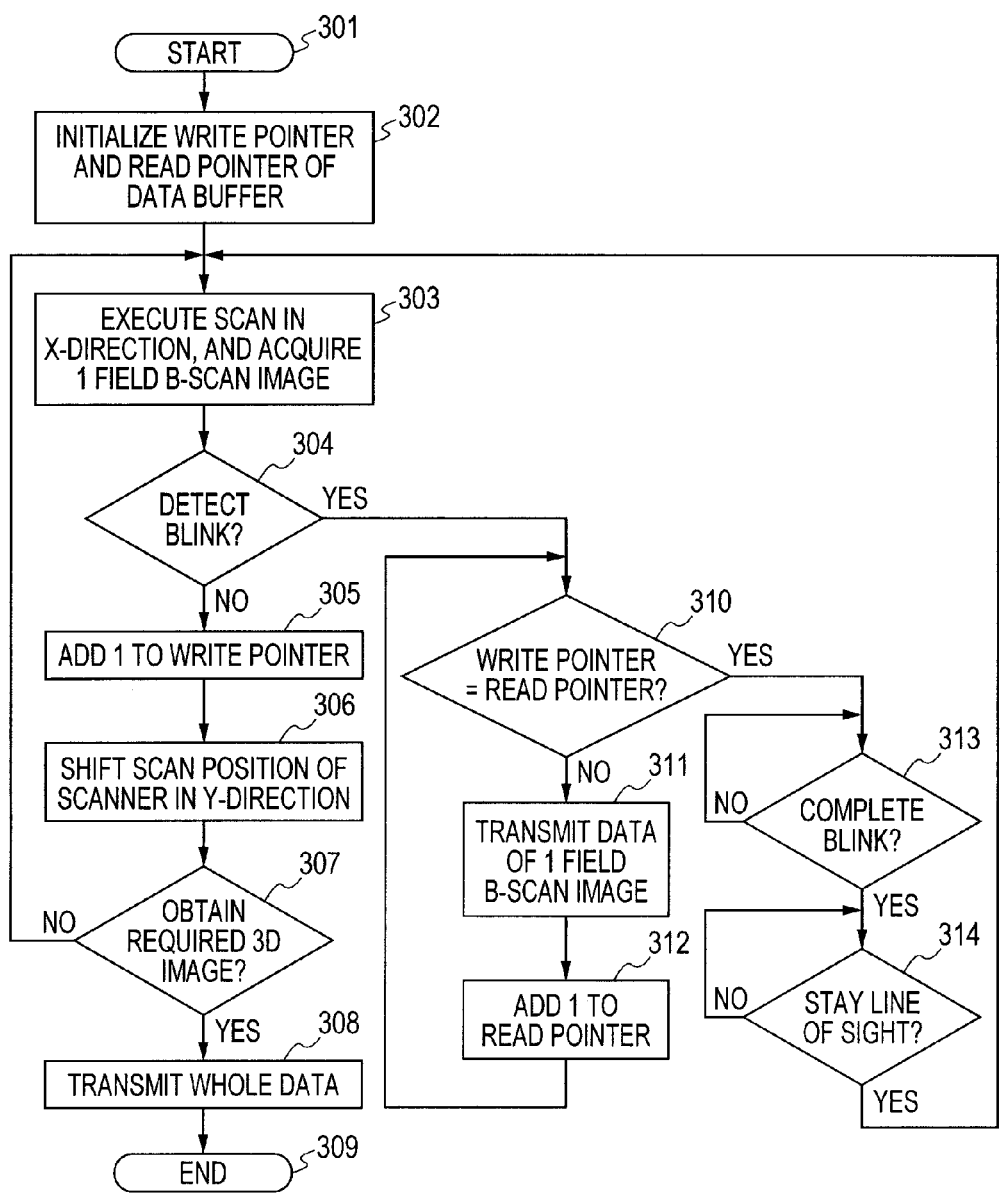
FIG. 7 is a flow chart illustrating processing performed at the time of image acquisition by an image acquisition apparatus according to a third embodiment of the present invention.

FIG. 7 is a flow chart of processing operation according to this embodiment. A block diagram of an entire system of an image acquisition apparatus and a timing chart of the processing operation according to this embodiment are the same as those in the first embodiment, and hence illustration and description thereof are herein omitted.

After the image taking is started in Step 301 of FIG. 7, in Step 302, both a write pointer and a read pointer of the data buffer are initialized. The write pointer indicates a location of the B-scan image in the data buffer for which the image taking has been performed without any blink. Further, the read pointer indicates a location in the data buffer which is to be subjected to the data transmission to the PC. In Step 303, the scanner executes the scan in the X-direction to acquire a B-scan image for one field. In Step 304, it is detected whether or not a blink has occurred. When no blink has occurred while acquiring the B-scan image for one field, 1 is added to the write pointer in Step 305, and the scanning point of the scanner is shifted in the Y-direction in Step 306. In Step 307, it is checked whether or not the image acquisition has been completed. When the image acquisition has not been completed, the processing returns to Step 303. When the image acquisition has been completed, all pieces of the B-scan data are transmitted to the PC in Step 308, and the processing is finished in Step 309.

When it is detected in Step 304 that a blink has occurred, it is checked in Step 310 whether or not the write pointer coincides with the read pointer. When the write pointer does not coincide with the read pointer, this means that there exists B-scan data to be transmitted from the data buffer to the PC, and hence, in Step 311, data corresponding to one B-scan field is transmitted from the data buffer to the PC. Then, in Step 312, 1 is added to the read pointer, and the processing returns to Step 310. In other words, through the processing from Steps 310 to 312, only the B-scan data obtained when no blink has occurred can be transmitted to the PC on a field basis.

When the write pointer coincides with the read pointer in Step 310, this means that there exists no B-scan data to be transmitted from the data buffer to the PC. Thus, it is checked in Step 313 whether or not the blink has been completed, and it is then checked in Step 314 whether or not the line of sight has become stable. After that, the processing returns to Step 303.

With the operation described above, according to this embodiment, only the B-scan data obtained when no blink has occurred is transmitted to the PC on a field basis, and hence the load imposed on the PC can be reduced. In this embodiment, the description has been given by taking a case where a single data buffer is provided. However, it is to be understood that even when multiple data buffers are provided, only the B-scan data obtained when no blink has occurred can be transmitted to the PC on a field basis.

Further, by appropriately changing the state (color, shape, etc.) of a fixation lamp, which is usually used to stabilize the line of sight, by a changing unit, for example, a subject may be prompted to blink, with the result that the above-mentioned effects can be acquired more reliably. In this case, the detection unit may be configured to detect the blink of the eye to be inspected, based on the change in state of the fixation lamp which is made by the changing unit.

With this, even when an eye to be inspected which has a long interblink interval is targeted, the image taking can be performed without suspending the image taking and the transmission, and as a result, the time period required for the image taking can be reduced.

(Another Embodiment)

Further, the present invention may be realized by executing the following processing as well. Specifically, in the processing, software (program) for implementing the functions of the embodiments described above is supplied to a system or an apparatus via a network or various kinds of storage media, and a computer of the system or the apparatus (or CPU, MPU, etc.) reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-161373, filed Jul. 16, 2010, and Japanese Patent Application No. 2011-139041, filed Jun. 23, 2011, which are hereby incorporated by reference herein in their entirety.

What is claimed is:

1. An image acquisition apparatus, comprising:
an acquisition unit for acquiring a tomographic image of an eye to be inspected;
a transmitting unit for transmitting the tomographic image to an external apparatus;
a storing unit for storing the acquired tomographic image;
a detection unit for detecting a blink of the eye to be inspected while acquiring the tomographic image; and
a control unit for controlling the transmitting unit to transmit the tomographic image stored in the storing unit to the external apparatus when the detection unit detects the blink of the eye to be inspected.

2. An image acquisition apparatus according to claim 1, wherein the acquisition unit comprises:
an interference unit for causing interference between a return light returning from a fundus of the eye to be inspected and a reference light;
a light receiving unit for receiving an interference beam from the interference unit; and
a generation unit for generating the tomographic image based on the interference beam received by the light receiving unit.

3. An image acquisition apparatus according to claim 1, wherein, when the blink is detected, the control unit controls the acquisition unit to suspend the acquisition of the tomographic image.

4. An image acquisition apparatus according to claim 3, wherein the detection unit detects completion of the blink, and
wherein, when the detection unit detects the completion of the blink of the eye to be inspected, the control unit controls the acquisition unit to resume the acquisition of the tomographic image.

5. An image acquisition apparatus according to claim 4, wherein, when the completion of the blink is detected, the control unit controls the acquisition unit to resume the acquisition of the tomographic image after a lapse of a predetermined period.

6. An image acquisition apparatus according to claim 1, further comprising a scan unit for scanning a light on a fundus of the eye to be inspected,
wherein, when the detection unit detects a completion of the blink, the control unit controls the scan unit to resume the acquisition of the tomographic image based on a point at which the scan unit has suspended the scanning of the light on the fundus of the eye to be inspected.

7. An image acquisition apparatus according to claim 6, further comprising a judgment unit for judging whether or not the acquisition of the tomographic image is to be resumed based on the point at which the scanning of the light by the scan unit has been suspended,
wherein, when the judgment unit judges that the acquisition of the tomographic image is to be resumed, the control unit controls the acquisition unit to resume the acquisition of the tomographic image.

8. An image acquisition apparatus according to claim 7, further comprising a determination unit for determining, when the judgment unit judges that the acquisition of the tomographic image is to be resumed, another sub scanning point of the scan unit, from which the acquisition of the tomographic image is to be resumed, based on the sub scanning point.

9. An image acquisition apparatus according to claim 1, wherein, when the tomographic image is transmitted to the external apparatus, the tomographic image obtained in a case where no blink occurs is transmitted one by one.

10. An image acquisition apparatus according to claim 1, further comprising:
a fixation lamp for fixing the eye to be inspected; and
a changing unit for changing a state of the fixation lamp so as to prompt the blink of the eye to be inspected,
wherein the detection unit detects the blink of the eye to be inspected, based on the change in the state of the fixation lamp.

11. A control method for an image acquisition apparatus, comprising the steps of:
acquiring a tomographic image of an eye to be inspected;
storing the acquired tomographic image in a storing unit;
detecting a blink of the eye to be inspected while acquiring the tomographic image; and
transmitting the tomographic image stored in the storing unit to an external apparatus when the blink of the eye to be inspected is detected in the detecting.

12. A non-transitory computer-readable storage medium having a program stored therein, the program causing a computer to perform the control method according to claim 11.

13. An image acquisition apparatus, comprising:
an acquisition unit for acquiring a tomographic image of an eye to be inspected;
a scan unit for scanning a light on a fundus of the eye to be inspected;
a detection unit for detecting a blink of the eye to be inspected; and
a control unit for controlling the scan unit so that the acquisition of the tomographic image is resumed, after the scan unit suspends a scanning of the light, based on a point at which the scanning has been suspended when the detection unit detects the blink of the eye to be inspected.

14. An image acquisition apparatus according to claim 13, further comprising a judgment unit for judging whether or not the scanning of the light for acquiring the tomographic image is to be resumed based on the point at which the scanning of the light has been suspended,
wherein, when the judgment unit judges that the acquisition of the tomographic image is to be resumed, the control unit controls the acquisition unit to resume the acquisition of the tomographic image.

15. An image acquisition apparatus according to claim 14, further comprising a determination unit for determining, when the judgment unit judges that the acquisition of the tomographic image is to be resumed, another sub scanning point of the scan unit, from which the acquisition of the tomographic image is to be resumed, based on the sub scanning point.

16. A control method for an image acquisition apparatus, comprising the steps of:
- acquiring a tomographic image of an eye to be inspected;
- scanning a light on a fundus of the eye to be inspected, by a scan unit;
- detecting a blink of the eye to be inspected; and
- suspending a scanning of the light, when the detection unit detects the blink of the eye to be inspected; and
- controlling, based on a point at which the scanning has been suspended, the scan unit so that the acquisition of the tomographic image is resumed.

17. A control method for an image acquisition apparatus according to claim 16, further comprising a step of judging whether or not the scanning of the light for acquiring the tomographic image is to be resumed based on the point at which the scanning of the light has been suspended, wherein, when it is judged that the acquisition of the tomographic image is to be resumed, the acquisition of the tomographic image is resumed.

18. A control method for an image acquisition apparatus according to claim 16, further comprising a step of determining, when it is judged that the acquisition of the tomographic image is to be resumed, another sub scanning point of the scanning the light, from which the acquisition of the tomographic image is to be resumed, based on the sub scanning point.

19. A non-transitory computer-readable storage medium having recorded thereon a program for causing a computer to perform steps of the control method according to claim 16.

* * * * *